(12) United States Patent
Conder et al.

(10) Patent No.: US 9,844,653 B2
(45) Date of Patent: Dec. 19, 2017

(54) VASCULAR OCCLUDER WITH CROSSING FRAME ELEMENTS

(71) Applicant: COOK MEDICAL TECHNOLOGIES LLC, Bloomington, IN (US)

(72) Inventors: Andrew W. Conder, Bloomington, IN (US); John R. LeBlanc, Bloomington, IN (US); David N. Marker, Borup (DK); Susan Gall Sahlgren, Copenhagen (DK); Casper Herdahl, Nykoebing Falster (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 280 days.

(21) Appl. No.: 14/516,071

(22) Filed: Oct. 16, 2014

(65) Prior Publication Data

US 2015/0105814 A1    Apr. 16, 2015

(30) Foreign Application Priority Data

Oct. 16, 2013    (GB) ............................... GB1318306.6

(51) Int. Cl.
*A61B 17/12*    (2006.01)
*A61M 29/00*    (2006.01)

(52) U.S. Cl.
CPC ....... *A61M 29/00* (2013.01); *A61B 17/12109* (2013.01); *A61B 17/12172* (2013.01); *A61M 2205/04* (2013.01)

(58) Field of Classification Search
CPC ........ A61B 17/12022; A61B 17/12027; A61B 17/12031; A61B 17/12036;

(Continued)

(56) References Cited

U.S. PATENT DOCUMENTS

| 4,662,885 A | * | 5/1987 | DiPisa, Jr. ................ A61F 2/01 623/1.25 |
| 4,957,501 A | * | 9/1990 | Lahille ..................... A61F 2/01 128/899 |

(Continued)

FOREIGN PATENT DOCUMENTS

| WO | WO 01/56500 A2 | 8/2001 |
| WO | WO 2008/115922 A1 | 9/2008 |
| WO | WO 2012/051489 A2 | 4/2012 |

OTHER PUBLICATIONS

European Patent Office Communication for EP 14275219.5-1654 dated Mar. 7, 2016.

(Continued)

*Primary Examiner* — Ryan J Severson
(74) *Attorney, Agent, or Firm* — Brinks Gilson & Lione (57) ABSTRACT

An occlusion device includes first and second crossing frame elements each of annular ring-shape, as well as first and second annular support elements connected to respective extremities of the crossing frame elements. The frame and support elements are provided with covers made of a substantially impervious material. The occluder may include a covering sleeve of stretchable material. The occluder substantially stops or reduces the flow of blood therethrough, creating blood statis and subsequent occlusion by clot formation within the occluder. The structure of the frame elements ensures good edge sealing and enhanced fixation of the occluder in a vessel as blood pressure impinges upon the covers of the occluder.

21 Claims, 3 Drawing Sheets

(58) Field of Classification Search
CPC .......... A61B 17/1204; A61B 17/12099; A61B 17/12109; A61B 17/12113; A61B 17/12131; A61B 17/1214; A61B 17/12145; A61B 17/12215; A61B 17/12168; A61B 17/12172; A61B 17/12177; A61M 29/00
See application file for complete search history.

(56) References Cited

U.S. PATENT DOCUMENTS

| | | | | |
|---|---|---|---|---|
| 5,108,419 | A * | 4/1992 | Reger | A61B 17/320725 606/159 |
| 5,350,398 | A * | 9/1994 | Pavcnik | A61F 2/01 606/200 |
| 5,375,612 | A * | 12/1994 | Cottenceau | A61F 2/01 128/899 |
| 5,443,478 | A * | 8/1995 | Purdy | A61B 17/12022 604/907 |
| 5,527,338 | A * | 6/1996 | Purdy | A61B 17/12022 606/108 |
| 5,683,411 | A * | 11/1997 | Kavteladze | A61B 17/0057 606/200 |
| 5,693,067 | A * | 12/1997 | Purdy | A61B 17/12022 128/899 |
| 5,733,294 | A * | 3/1998 | Forber | A61B 17/12022 606/151 |
| 5,766,219 | A * | 6/1998 | Horton | A61B 17/12022 606/151 |
| 5,792,155 | A | 8/1998 | Van Cleef | |
| 5,895,410 | A * | 4/1999 | Forber | A61B 17/12022 606/191 |
| 6,063,113 | A * | 5/2000 | Kavteladze | A61B 17/0057 606/200 |
| 6,152,144 | A * | 11/2000 | Lesh | A61B 17/0057 128/898 |
| 6,355,052 | B1 * | 3/2002 | Neuss | A61B 17/0057 606/213 |
| 6,361,545 | B1 * | 3/2002 | Macoviak | A61B 17/12136 606/151 |
| 6,368,338 | B1 * | 4/2002 | Konya | A61B 17/12022 606/200 |
| 6,554,849 | B1 * | 4/2003 | Jones | A61B 17/12022 606/200 |
| 6,638,257 | B2 * | 10/2003 | Amplatz | A61B 17/12022 604/200 |
| 6,652,556 | B1 * | 11/2003 | VanTassel | A61B 17/12122 606/200 |
| 7,331,976 | B2 * | 2/2008 | McGuckin, Jr. | A61F 2/013 606/113 |
| 7,347,869 | B2 * | 3/2008 | Hojeibane | A61F 2/2418 606/200 |
| 7,582,100 | B2 * | 9/2009 | Johnson | A61F 2/01 210/435 |
| 7,604,661 | B2 * | 10/2009 | Pavcnik | A61F 2/01 623/1.24 |
| 7,785,343 | B2 * | 8/2010 | Johnson | A61F 2/01 606/200 |
| 7,789,892 | B2 * | 9/2010 | Johnson | A61F 2/01 606/200 |
| 7,854,747 | B2 * | 12/2010 | Johnson | A61F 2/01 606/200 |
| 7,972,359 | B2 * | 7/2011 | Kreidler | A61B 17/0057 606/200 |
| 8,226,679 | B2 * | 7/2012 | Johnson | A61F 2/01 210/435 |
| 8,262,691 | B2 * | 9/2012 | McGuckin, Jr. | A61F 2/013 606/200 |
| 8,308,752 | B2 * | 11/2012 | Tekulve | A61B 17/12022 606/200 |
| 8,617,205 | B2 * | 12/2013 | Pavcnik | A61B 17/0057 606/151 |
| 8,679,148 | B2 * | 3/2014 | McGuckin, Jr. | A61F 2/013 606/200 |
| 8,728,112 | B2 * | 5/2014 | Evert | A61B 17/12022 606/200 |
| 9,211,123 | B2 * | 12/2015 | Bastin | A61B 17/12022 |
| 9,289,280 | B2 * | 3/2016 | Tafti | A61F 2/01 |
| 9,314,259 | B2 * | 4/2016 | Johnson | A61B 17/221 |
| 9,332,977 | B2 * | 5/2016 | Pavcnik | A61B 17/0057 |
| 2001/0039450 | A1 * | 11/2001 | Pavcnik | A61F 2/01 623/1.24 |
| 2002/0029051 | A1 * | 3/2002 | Callister | A61B 17/12022 606/157 |
| 2002/0099437 | A1 * | 7/2002 | Anson | A61B 17/0057 623/1.15 |
| 2002/0183783 | A1 * | 12/2002 | Shadduck | A61F 2/013 606/200 |
| 2003/0028213 | A1 * | 2/2003 | Thill | A61B 17/0057 606/200 |
| 2003/0171774 | A1 * | 9/2003 | Freudenthal | A61B 17/0057 606/213 |
| 2003/0212429 | A1 * | 11/2003 | Keegan | A61F 2/01 606/200 |
| 2004/0143277 | A1 * | 7/2004 | Marino | A61B 17/0057 606/157 |
| 2004/0186558 | A1 | 9/2004 | Pavcnik et al. | |
| 2004/0236368 | A1 * | 11/2004 | McGuckin, Jr. | A61F 2/013 606/200 |
| 2005/0228434 | A1 * | 10/2005 | Amplatz | A61B 17/0057 606/200 |
| 2006/0020286 | A1 * | 1/2006 | Niermann | A61F 2/01 606/200 |
| 2006/0111770 | A1 * | 5/2006 | Pavcnik | A61B 17/12022 623/1.13 |
| 2006/0235463 | A1 * | 10/2006 | Freudenthal | A61B 17/0057 606/200 |
| 2006/0241677 | A1 * | 10/2006 | Johnson | A61F 2/01 606/200 |
| 2006/0241678 | A1 * | 10/2006 | Johnson | A61F 2/01 606/200 |
| 2006/0241679 | A1 * | 10/2006 | Johnson | A61F 2/01 606/200 |
| 2007/0123932 | A1 * | 5/2007 | Gray | A61F 2/01 606/200 |
| 2008/0021497 | A1 * | 1/2008 | Johnson | A61F 2/01 606/200 |
| 2008/0097586 | A1 * | 4/2008 | Pavcnik | A61F 2/01 623/1.24 |
| 2008/0147111 | A1 * | 6/2008 | Johnson | A61F 2/01 606/200 |
| 2010/0217381 | A1 | 8/2010 | Paul et al. | |
| 2010/0280588 | A1 | 11/2010 | Schreck | |
| 2010/0324590 | A1 * | 12/2010 | Johnson | A61F 2/01 606/200 |
| 2011/0160753 | A1 * | 6/2011 | Bastin | A61B 17/12022 606/153 |
| 2012/0179196 | A1 * | 7/2012 | Johnson | A61F 2/01 606/200 |
| 2013/0035715 | A1 * | 2/2013 | Johnson | A61F 2/01 606/200 |
| 2013/0184744 | A1 * | 7/2013 | Johnson | A61F 2/01 606/200 |
| 2013/0190804 | A1 * | 7/2013 | Johnson | A61F 2/01 606/200 |
| 2013/0282043 | A1 * | 10/2013 | Johnson | A61F 2/01 606/200 |
| 2013/0282044 | A1 * | 10/2013 | Johnson | A61F 2/01 606/200 |
| 2013/0282045 | A1 * | 10/2013 | Johnson | A61F 2/01 606/200 |
| 2013/0289519 | A1 * | 10/2013 | Johnson | A61F 2/01 604/500 |
| 2013/0289609 | A1 * | 10/2013 | Johnson | A61F 2/01 606/200 |
| 2013/0289610 | A1 * | 10/2013 | Johnson | A61F 2/01 606/200 |

(56) References Cited

U.S. PATENT DOCUMENTS

| | | | | |
|---|---|---|---|---|
| 2013/0289611 A1* | 10/2013 | Johnson | .................... | A61F 2/01 |
| | | | | 606/200 |
| 2013/0296918 A1* | 11/2013 | Johnson | .................... | A61F 2/01 |
| | | | | 606/200 |
| 2015/0164630 A1* | 6/2015 | Johnson | .................... | A61F 2/01 |
| | | | | 606/200 |
| 2015/0173884 A1* | 6/2015 | Johnson | .................... | A61F 2/01 |
| | | | | 606/200 |
| 2016/0074025 A1* | 3/2016 | Bastin | .............. | A61B 17/12022 |
| | | | | 606/198 |

OTHER PUBLICATIONS

Extended European Search Report for EP14275219.5 dated Mar. 20, 2015.

\* cited by examiner

VASCULAR OCCLUDER WITH CROSSING FRAME ELEMENTS

CROSS-REFERENCE TO RELATED APPLICATION

This application claims the benefit of priority under 35 U.S.C. §119(a) to Great Britain Patent Application No. 1318306.6, filed Oct. 16, 2013, which is incorporated by reference here in its entirety.

TECHNICAL FIELD

The present invention relates to a vascular occlusion device for use in veins or arteries.

BACKGROUND ART

There are several medical indications for which vascular occlusion is an appropriate treatment including, for example, for rerouting blood to a different part of a patient's body, for reducing or halting supply of blood to a tumour or other growth, for reducing the supply of blood to an organ or area of a patient's body prior to a medical procedure or treatment, for reducing pressure on a fistular, weakened or leaking blood vessel, and so on.

Conventionally, vascular occlusion was effected by surgically closing or ligating the blood vessel, which required an open surgical procedure with inherent risks and complications. More recently, vascular occlusion has been effected by the endoluminal implantation into a patient of one or more implantable medical devices. A well-known device is in the form of a wire coil which can be implanted in a patient's vasculature and which effects occlusion by promoting embolization of blood, usually by means of fibres attached along the length of the wire coil. Typically, several such coils are implanted, one adjacent the other in the vessel, until the clinician is satisfied that adequate occlusion has been achieved. Such a procedure can take time to reach adequate occlusion. Moreover, the length of the occluding barrier produced by the implanted coils will vary in dependence upon the number of coils implanted and the size of the vessel. This is not, though, always practicable.

It is also known to effect occlusion by administration of a thrombogenic agent into a patient, for instance by injection of such agent between two spaced balloons which are inflated in a patient's vessel. The thrombogenic agent assists in the creation of a blood clot between the inflated balloons, which can then be removed so as not to leave in the patient's body any foreign device. The balloons can also provide an occluding barrier of predetermined length, suitable for locations where there is limited vascular space.

As well as issues of length of the occluding barrier which may be necessary, and thus of accommodation in a patient's vasculature, occlusion can also be prone to recanalization, that is to leakage through the occluding barrier and eventual reopening of the vessel. Such shortcomings can occur with the devices and methods described above.

Vascular occluders can also suffer from migration within the vessel, caused by the pressure of blood on the occluder, as well as by changes in the size and shape of the vessel over time and during normal bodily functioning. Migration can result in loss of the occlusion seal, and thus of blood leakage past the occluder, blockage of unwanted vessels including side branches, and so on.

SUMMARY OF THE INVENTION

The present invention seeks to provide an improved vascular occluder.

According to an aspect of the present invention, there is provided a vascular occlusion device for use in occluding a body vessel, the device having first and second ends and sides, and including: first and second frame elements made of a resilient material, the first and second frame elements being coupled to one another in crossing relationship; the first and second frame elements extending to the proximal and distal ends and sides of the device; and proximal and distal end covers extending across the proximal and distal ends of the device.

The crossing arrangement of the first and second frame elements and their orientation in the device together with the provision of the end covers provides, as explained in detail below, a structure which can expand reliably in a vessel and which generates an opening force when subjected to fluid pressure. This enhances the fit of the device in the vessel, enhances the seal of the device against to vessel walls and reduces the chance of migration of the device. The structure is also in operational condition over a range of opening diameters, making the device suitable for deployment in a range of vessel sizes.

In the preferred embodiment, the device has a longitudinal dimension extending between the proximal and distal ends of the device, and at least the proximal cover extends substantially orthogonally to this longitudinal dimension. With this orientation, the upstream cover will be orthogonal to the fluid flow and will therefore absorb the full force of that flow. This will have the effect of generating a force on the frames tending to cause them to flatten or expand radially outwardly, thereby to press further against the vessel walls and thus to enhance the fit and seal.

Advantageously, both the proximal and the distal covers extend substantially orthogonally to the longitudinal dimension. Thus, the device could be used in either orientation in the vessel, facilitating its fitting in a delivery assembly and facilitating deployment.

The first and second frame elements are preferably disposed at an angle of at least 30 degrees to one another, more preferably at an angle of at least 45 degrees to one another, most preferably at an angle of less than 90 degrees to one another. Having an angle of less than 90 degrees ensures that the device retains a length which is greater than its width, useful in ensuring correct orientation of the device in a vessel.

The first and second frame elements are advantageously ring-shaped prior to any bending or stretching of the device, which gives them a shape which is naturally in conformance with the shape of the vessel.

Preferably, the first and second frame elements cross at mid-points thereof.

In the preferred embodiments, the first and second frame elements are fixed to one another in this crossing relationship. The first and second frame elements may be integral with another, for instance being formed as a unitary structure or by being woven, braided or knitted into each other, although could also be bonded or welded to one another.

In an embodiment, at least one of the proximal and distal end covers is porous. In another embodiment, at least one of the proximal and distal end covers is made of impermeable material.

It is preferred that the first and second frame elements are formed of one of spring material and shape-memory material.

Advantageously, the device includes cover supports supporting the proximal and distal end covers. The cover supports may be in the form of support rings coupled to the first and second frame elements.

In the preferred embodiment, the device includes a frame cover element extending across each of the first and second frame elements. The provision of additional cover elements creates a number of chambers within the device, in which blood can stagnate and over time coagulate to form additional occlusion barriers or plugs.

Preferably, the first and second frame elements and associated cover elements provide tapering chambers from the proximal and distal ends of the device to a centre of the device.

The device advantageously includes a sleeve extending around the device and along the longitudinal dimension thereof. The sleeve may be made of porous or impermeable material. Preferably, the sleeve is made of a stretchable material or structure to allow radial expansion thereof.

In the preferred embodiment, the device is generally cylindrical.

Also described herein is a method of occluding a body vessel by means of a device having first and second ends and sides, and including:

first and second frame elements made of a resilient material, the first and second frame elements being coupled to one another in crossing relationship; the first and second frame elements extending to the proximal and distal ends and sides of the device; and proximal and distal end covers extending across the proximal and distal ends of the device;

the method including the steps of:

deploying the device endoluminally in a vessel from a radially contracted configuration;

allowing the device to expand radially such that the first and second ends of the device are located along the vessel, wherein blood pressure in the vessel presses on the first sand second frame elements biasing these to a widening configuration, thereby to bias the device towards an increased diameter.

Other features of the device and method disclosed herein will become apparent from the following specific description of preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There are described below various embodiments of occluder device according to the teachings herein. It is to be understood that the drawings are schematic only and are not to scale. They show the principal elements of the device, including its structure and the components forming the structure, as well as its intended implementation within a vessel of a patient, although do not disclose commonplace elements such as anchoring barbs, radiopaque markers and the like. The skilled person will appreciate that the relative sizes of the various elements of the device will be dependent upon choice and the size of the vessel in which the device is to be used, as well as upon the particular materials chosen for the various elements of the device. The skilled person will appreciate that the drawings do disclose structural features and form an integral part of the disclosure of this patent specification.

Figure 1:
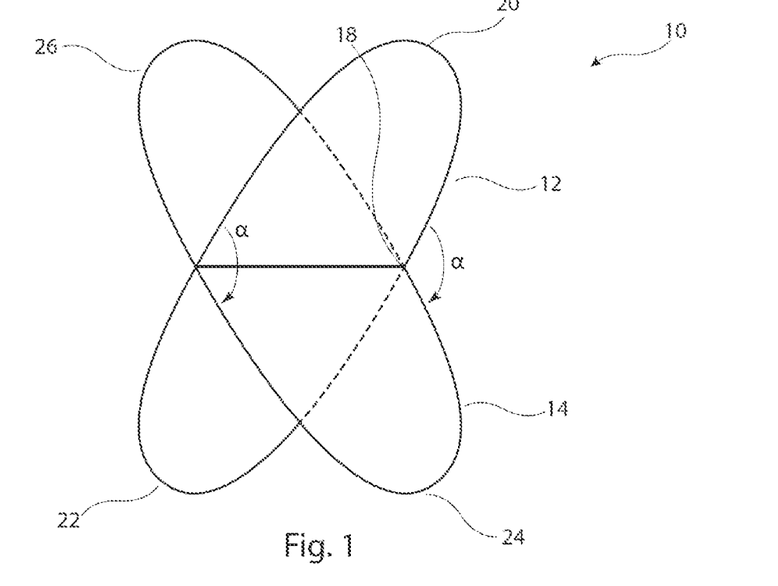
FIG. 1 shows the crossing frame of a preferred embodiment of occluder.
Figure 2:
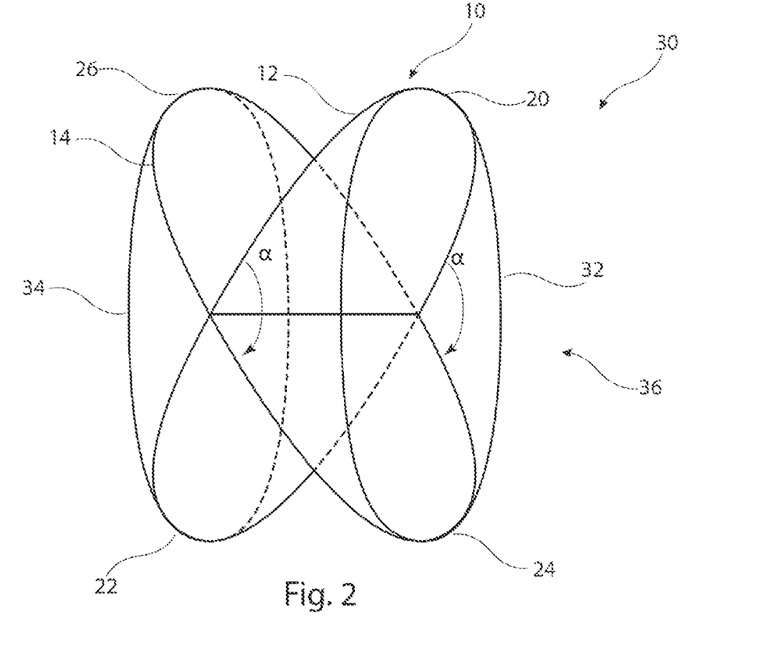
FIG. 2 shows the crossing frame of FIG. 1 to which are attached end supports.
Figure 3:
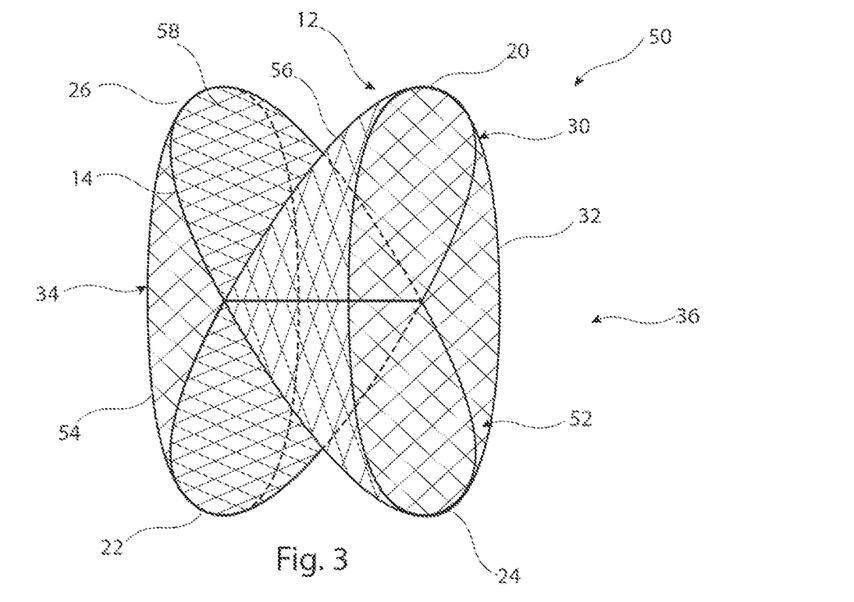
FIG. 3 shows the structure of FIG. 2 with covers provided on the crossing frames and end supports.
Figure 4:
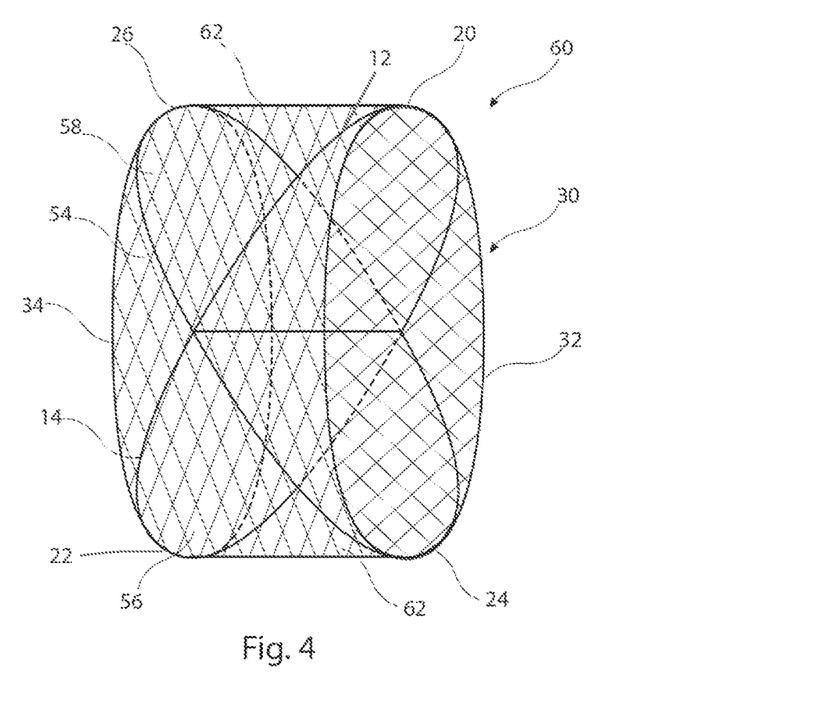
FIG. 4 shows the structures of FIGS. 1 to 3 provided also with a cylindrical sleeve.
Figure 5:
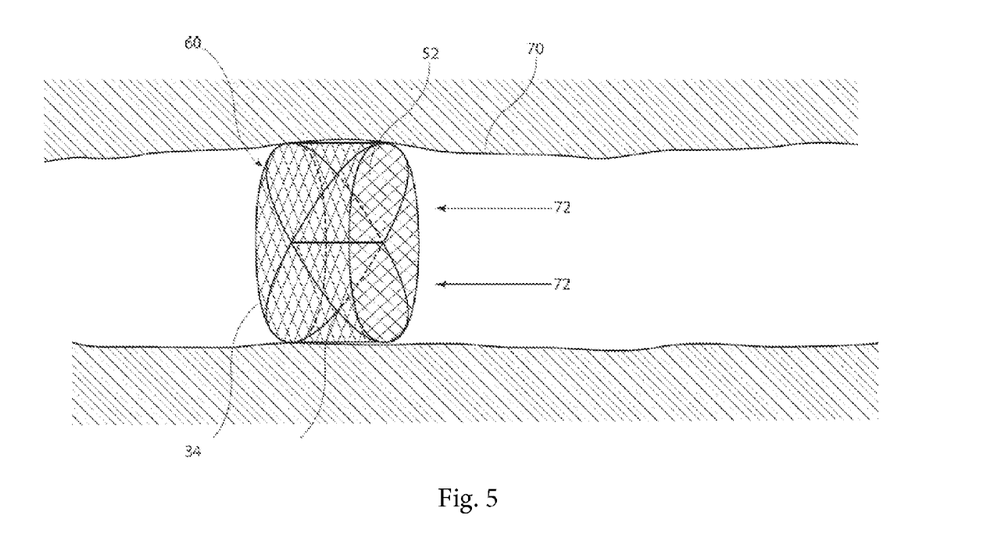
FIG. 5 shows the device of FIG. 4 deployed in a vessel.

FIGS. 1 to 3 can be said to show various parts of the occluder in its most complete form, although these Figures also show more simplified versions of the device with respect to the preferred embodiment shown in FIGS. 4 and 5.

Referring first to FIG. 1, this shows the basic frame 10 of the occluder device. This includes first and second frame elements 12, 14, which in this embodiment are each in the shape of a ring of resilient material. The frame elements 12, 14 may be made from a spring material, for example, stainless steel, or a shape memory material such as a shape memory alloy, preferably Nitinol. The frame elements 12, 14 are coupled to one another at diametrically opposing points 16, 18, so as to be disposed relative to one another at an angle α. In a preferred embodiment, the frame elements 12, 14 are fixed to one another at the points 16, 18, for example by being woven, knitted or braided into each other. In other embodiments they may be bonded or welded together, or be integrally formed as a unitary structure.

In some embodiments, the frame elements 12, 14, are not fixed to one another but maintain the orientation shown in FIG. 1 by means of other structural elements forming the occluder, as can be seen for instance with the embodiments shown in the following drawings. These could be, for example, the end supports shown in the embodiments of FIGS. 2 and 3 and also, or in the alternative, the covering cylindrical sleeve shown in the embodiments of FIGS. 4 and 5.

The frame elements 12, 14 are preferably disclosed at an angle α of at least 30° to one another at what could be described as the front face of the frame 10, as will become apparent below. In other embodiment the frame elements 12, 14 may be disposed at an angle α of at least 45° to one another and preferably less than around 90°. Having an angle of less than 90 degrees ensures that the structure 10 remains longer than wider, thereby ensuring that the device is deployed and remains in the correct orientation in the vessel.

Each of the frame elements 12, 14 is preferably substantially circular when viewed in plan, such that the frame 10 when viewed from its front face has a substantially round perimeter.

The front face of the frame 10, as with all the embodiments of device disclosed herein, faces the flow of blood within a vessel.

As can be seen in FIG. 1, each frame element includes extremities or ends 20 to 26 which in practice are located at the ends of the occluder device. In this regard, the ends 20, 24 of the frames 12, 14 are located at a first or proximal end of the frame 10 and in practice at the front face of the device. The ends 22, 26 are located at the second or distal end of the frame 10 and in practice at the distal end of the device.

The frame 10 forms the basic frame structure of the embodiments of the occluder device shown in the subsequent Figures.

Referring now to FIG. 2, this shows an embodiment of complete frame structure 30 which comprises the frame 10 of FIG. 1, with its crossing frame elements 12, 14. The frame structure 30 includes also support elements 32, 34 which support proximal and distal end covers to the occluder, the latter being described below and shown in the subsequent drawings. The support elements 32, 34 are preferably in the form of annular rings which are substantially circular when viewed in plan. They are made of a resilient material, such as a spring material or shape memory material and are preferably of the same material as the frame elements 12, 14. It is not excluded, however, that the support elements 32, 34 could be made from a different material to that of the frame elements 12, 14. For instance, they could be made of spring steel, whereas the frame elements 12, 14 could be made of a shape memory material, or vice versa.

In an embodiment, the support elements 32, 34 could have the form of stent rings, for instance being sinusoidal or zigzag ring structures.

The support elements 32, 34 are preferably fixed to their respective ends 20, 24 or 22, 26 of the frame elements 12 and 14 respectively, such as to form an integral structure with the frame elements 12 and 14. The support elements 32 and 34 could be fixed to the frame elements 12 and 14 by wrapping, weaving or braiding, but could equally be sutured together with thread. In other embodiments they could be bonded or welded together.

As with the embodiment of FIG. 1, the frame elements 12, 14 are disposed at an angle α to one another and the support elements 32 and 34 are preferably parallel to one another. The frame element 32, in this embodiment forms the front face 36 of the frame 30 and in practice of the occluder.

The frame elements 12 and 14 are preferably of the same shape and size. Similarly, the support elements 32 and 34 are preferably also of the same size. It is not excluded, however, that the support elements 32 and 34, and consequentially the frame elements 12 and 14, may not be of the same size so as to give the frame 30 a tapering form, useful for example in deployment in a tapering vessel. It is preferred however, that the frame 30 is entirely symmetrical about its centre point.

It is preferred also that the support elements 32, 34 have diameters the same as the diameter of the frame elements 12, 14, such that the point of widest diameter crosswise of the support elements 32, 34 is substantially the same as the distance between the diameter of the opposing points 16 and 18 of the frame elements 12, 14.

Referring now to FIG. 3, there is a shown an embodiment of occlusion device 50 which includes the frame structure 30 of FIG. 2, that is the crossing frame elements 12 and 14 connected to the proximal and distal support elements 32 and 34.

The frame structure 30 is provided with a proximal cover 52 which extends across and is supported by the proximal support element 32. In similar manner, the distal support element 34 supports a distal cover 54, which is likewise fixed to and supported by the distal frame element 34. In this embodiment, the device 50 includes a further set of covers, a first cover 56 extending across and being supported by the first frame element 12 and a second cover 58 extending across and being supported by the second frame element 14.

The covers 52-58 may be fixed to their respective support elements 12, 14, 32 or 34 by bonding, by being sutured thereto, by being wrapped around the annular structure of the support elements or by any other method. They each preferably form a continuous cover across the area delimited by its respective support element, thereby to leave no openings or gaps.

The covers 52-58 are preferably made of the same material as one another but it is not excluded that they may be made of different materials, for example all being made of an impermeable material or with the covers 52, 54 being made of a permeable material and the covers 56 and 58 being made of an impermeable material.

The covers may be a mesh or woven fabric material, a synthetic material or a natural material, such as SIS. The covers could equally be made of permeable plates or sheets, for instance of braided wires.

The covers 52-58 should at least substantially slow down, preferably stop, the flow of blood through the occluder 50, thereby to create blood statis within the vessel. Stagnant or near stagnant blood will eventually coagulate and thus create an occlusion barrier in the form of a thrombus plug. It will be appreciated from a view of FIG. 3 that the structure of occluder 50, and in particular of the frame elements 12, 14, 32 and 34, creates a plurality of chambers within the volume of the occluder 50. In the particular example of FIG. 3 there are four chambers, each bounded by the covers 52-58 and also, in practice, by the vessel wall. Thus, the occluder provides a plurality of volumes or chambers within which blood can clot, thereby providing a plurality of occlusion barriers.

In a particular embodiment, the covers 52-58 may be finely porous, with pores formed by weaving or braiding a fibrous material or by fine pores or apertures in a sheet material. Such pores or apertures allow the passage of blood into the internal volume of the occluder 50 but at a substantially reduced blood flow which is practically static to promote thrombus formation. In this regard, it is preferred that all of the covers 52-58 are finely porous so that the entirety of the volume of the occluder 50 is eventually filled with blood.

Referring now to FIG. 4, there is shown an embodiment of occluder 60 which is very similar to the embodiment of occluder 50 of FIG. 3 and which includes, in addition to the frame structure 30 and covers 52-58, a cylindrical sleeve 62 which extends along the length of the occluder 60 from the proximal support element 32 to the distal support element 34. The sleeve 62 is preferably fixed to the support elements 32 and 34, in a manner similar to the covers 52-58.

The sleeve 62 is preferably made of an elastomeric material or other stretchable material able to expand upon radial expansion of the frame structure 30 of the occluder 60. Nickel titanium alloy such as Nitinol is a preferred material. The sleeve 62 may be made of a porous or impervious material. In some embodiments, the sleeve 62 may also be attached to the frame elements 12, 14, for example by bonding or heat welding, but this is not essential.

In some embodiments, the sleeve 62 could be a stent structure having a generally tubular shape and unitary structure, in which case the crossing frame 10 will reside within the tubular stent structure and be fixed to the inside of the lumen of the structure. In this case, the supports 32, 34 could include a membrane or permeable plates, usefully disposed at the ends of the tubular stent structure.

In other embodiments, the sleeve 62 could be a woven, knitted or braided structure, having a function equivalent to the tubular stent embodiment.

The primary purpose of the sleeve 62 is to provide support for the structure 60, in particular during its deployment within the vasculature of a patient. Especially when configured as a stent, the sleeve 62 can exert the required opening force on the device to hold it tight against the vessel wall. The sleeve 62 can also provide closed surfaces to the chambers within the occluder 60 irrespective of the effect of the vessel walls.

The use of a stretchable material or radially expandable component for the sleeve 62 also ensures that the sleeve 62 retains a substantially cylindrical form at different opening diameters of the occluder 60.

Referring now to FIG. 5, this shows the embodiment of occluder 60 of FIG. 4 deployed in a vessel 70 of a patient and as it would be used in practice. It will be apparent, with reference to FIG. 5 in particular, that the proximal/distal or front/back symmetry of the occluder 60 means that it can be deployed in a patient's vessel in any orientation, that is face on or back to front. In practice there is no difference between the front and the back of the occluder 60 (or of any of the other embodiments of occluder disclosed herein).

As can be seen in FIG. 5, the occluder 60 is deployed in a vessel such that the annular support elements 32, 34 expand to the width of the vessel 70 and abut against the vessel wall so as to hold the occluder 60 in place. The support elements 32, 34 preferably have a relaxed diameter which is larger than the diameter of the vessel 70 so as to apply a continuous opening or expansion force against the vessel walls, thereby to hold the occluder 60 in place.

When deployed in a vessel 70, blood flow 72 will press against the proximal occluder cover 52, which in practice will bias the cover 52 backwardly in the direction of the fluid pressure. However, the existence of the opposing annular support 34 and the crossing frame elements 12, 14 connected to the supports 32, 34 will result in the frame structure 30 of the occluder 60 tending to contract longitudinally and expand radially. This radial expansion force (caused by the pressing together of the crossing frame elements 12, 14) will increase the pressure applied by the frame structure 30 of the occluder 60 against the vessel walls and thereby enhance the fixing of the occluder 60 within the vessel and minimise the risk of migration of the occluder 70.

Furthermore, the structure provides good edge sealing of the occluder 60 to the vessel walls 70, the seal being enhanced when the occluder 60 is subjected to pressure from blood flow 72. This is also optimised by virtue of the fact that the frame 30, in combination also with the stretchable sleeve 62 in embodiments where this is provided, is able to expand to a range of diameters as a result of the flexibility of the frame structure 30, thereby ensuring that the annular support elements 32, 34 as well as the crossing frame elements 12, 14, expand smoothly to provide a good edge seal of the occluder 60 in vessels having a variety of diameters.

The device taught herein can be compressed for delivery through an introducer assembly of known form by radially compressing the frame structure 30, possible given that the frame elements 12, 14, 32, 34 are formed of a resilient material such as spring steel or shape memory material such as Nitinol. In some embodiments at least, the frame structure 30 can also be compressed radially by collapsing the frame elements 12, 14 towards a closed configuration, minimising angle α (alpha) between the two elements 12, 14, and then compressing the frame crossing points closer together. This will have the effect of radially compressing the frame structure 30 for delivery through an introducer sheath or catheter and will also lengthen the frame structure 30 as occurs with many endoluminally introduceable medical devices. The skilled person will understand the manners in which the device can be compressed for delivery.

It will also be appreciated, as described above, that the occluder could be formed without all of the covers shown in the embodiments of FIGS. 3-5 as one or more of these covers could be omitted while still retaining the occluder functionality of the device.

Although the support elements 32, 34 are shown as annular rings, these could be in the form of zigzag stent rings, as explained above, which are able to compress radially inwardly and expand radially outwardly by a pushing together and moving apart of the struts of the zigzag stent ring. The support elements 32, 34 could equally be made of any other radially expandable structure, including split rings and so on.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A vascular occlusion device for use in occluding a body vessel, the device including:
a first frame element and a second frame element made of a resilient material, wherein the first and second frame elements are annular, the first and second frame elements being coupled to one another in a crossing relationship; the first and second frame elements extending to a proximal end and a distal end of the device;
a proximal end cover and a distal end cover extending across the proximal and distal ends of the device; and
cover support elements that support the proximal and distal end covers; the cover support elements being in the form of annular rings and coupled to the first and second frame elements.

2. A vascular occlusion device according to claim 1, wherein the device has a longitudinal dimension extending between the proximal and distal ends of the device and includes at least the proximal cover extending orthogonally to said longitudinal dimension.

3. A vascular occlusion device according to claim 2, wherein both the proximal and the distal covers extend orthogonally to said longitudinal dimension.

4. A vascular occlusion device according to claim 3, wherein the first and second frame elements are disposed at an angle of at least 30 degrees to one another.

5. A vascular occlusion device according to claim 1, wherein the first and second frame elements are disposed at an angle of at least 45 degrees to one another.

6. A vascular occlusion device according to claim 1, wherein the first and second frame elements are disposed at an angle of less than 90 degrees to one another.

7. A vascular occlusion device according to claim 1, wherein the first and second frame elements each have a proximal extremity and a distal extremity opposite the proximal extremity, and wherein the proximal extremities of the first and second annular frames are spaced apart and the distal extremities of the first and second annular frames are spaced apart.

8. A vascular occlusion device according to claim 1, wherein the first and second frame elements cross at midpoints thereof.

9. A vascular occlusion device according to claim 1, wherein the first and second frame elements are fixed to one another in said crossing relationship at diametrically opposing points.

10. A vascular occlusion device according to claim 1, wherein the first and second frame elements are integral with another.

11. A vascular occlusion device according to claim 1, wherein at least one of the proximal and distal end covers is porous.

12. A vascular occlusion device according to claim 1, wherein at least one of the proximal and distal end covers is made of impermeable material.

13. A vascular occlusion device according to claim 1, wherein the first and second frame elements are formed of one of spring material and shape-memory material.

14. A vascular occlusion device according to claim 1, including a frame cover element extending across each of the first and second frame elements.

15. A vascular occlusion device according to claim 14, wherein the first and second frame elements and associated cover elements provide tapering chambers from the proximal and distal ends of the device to a center of the device.

16. A vascular occlusion device according to claim 1, including a sleeve extending around the device and in a longitudinal dimension thereof.

17. A vascular occlusion device according to claim 16, wherein the sleeve is made of porous or impermeable material.

18. A vascular occlusion device according to claim 16, wherein the sleeve is made of a stretchable material or structure to allow radial expansion thereof.

19. A vascular occlusion device according to claim 1, wherein the device is generally cylindrical.

20. A vascular occlusion device for use in occluding a body vessel, the device including:
a first frame element and a second frame element made of a resilient material, wherein the first and second frame elements each have a proximal extremity and a distal extremity opposite the proximal extremity, and wherein the proximal extremities of the first and second annular frames are spaced apart and the distal extremities of the first and second annular frames are spaced apart; the first and second frame elements being coupled to one another in a crossing relationship; the first and second frame elements extending to a proximal end and a distal end of the device;
proximal and distal end covers extending across the proximal and distal ends of the device; and
cover support elements that support the proximal and distal end covers; the cover support elements being in the form of annular rings and coupled to the first and second frame elements.

21. A vascular occlusion device for use in occluding a body vessel, the device including:
first and second frame elements made of a resilient material, the first and second frame elements being coupled to one another in a crossing relationship at diametrically opposing points; the first and second frame elements extending to a proximal end and a distal end of the device;
proximal and distal end covers extending across the proximal and distal ends of the device; and
cover support elements that support the proximal and distal end covers; the cover support elements being in the form of annular rings and coupled to the first and second frame elements.

* * * * *